United States Patent [19]

Saunders

[11] Patent Number: 6,131,266
[45] Date of Patent: Oct. 17, 2000

[54] METHOD AND APPARATUS FOR DIRECT LASER CUTTING OF METAL STENTS

[75] Inventor: Richard J. Saunders, Redwood City, Calif.

[73] Assignee: Advanced Cardiovascular Systems, Inc., Santa Clara, Calif.

[21] Appl. No.: 09/114,656

[22] Filed: Jul. 13, 1998

Related U.S. Application Data

[62] Division of application No. 08/783,698, Jan. 15, 1997, Pat. No. 5,780,807, which is a continuation of application No. 08/345,501, Nov. 28, 1994, abandoned.

[51] Int. Cl.[7] .............................. B23P 15/00; B23K 26/00
[52] U.S. Cl. .......................... 29/557; 29/558; 219/121.71
[58] Field of Search ................ 29/557, 558; 219/121.61, 219/121.71, 121.67

[56] References Cited

U.S. PATENT DOCUMENTS

| | | |
|---|---|---|
| 4,387,952 | 6/1983 | Slusher . |
| 4,733,665 | 3/1988 | Palmaz . |
| 4,963,022 | 10/1990 | Sommargren . |
| 4,994,071 | 2/1991 | MacGregor . |
| 5,073,694 | 12/1991 | Tessier et al. . |
| 5,102,417 | 4/1992 | Palmaz . |
| 5,345,057 | 9/1994 | Muller . |
| 5,569,295 | 10/1996 | Lam . |

FOREIGN PATENT DOCUMENTS

| | | |
|---|---|---|
| 0 221 570 A1 | 5/1987 | European Pat. Off. . |
| 0 364 787 A1 | 4/1990 | European Pat. Off. . |
| 0 421 729 A2 | 4/1991 | European Pat. Off. . |
| 2 070 490 | 9/1981 | United Kingdom . |
| WO 92/06734 | 4/1992 | WIPO . |

OTHER PUBLICATIONS

Brochure: *Industrial Strength Laser Marking: Turning Photons Into Dollars*, printed by Excel/Control Laser, Inc. (1992).

Brochure: *Anomatic™ II Positioning Controller*, printed by Anorad Corporation (Undated).

*Primary Examiner*—Irene Cuda
*Attorney, Agent, or Firm*—Fulwider Patton Lee & Utecht, LLP

[57] ABSTRACT

An improved method of making expandable stent for implantation in a body lumen, such as an artery, from a single length of tubing. The stent consists of a plurality of radially expandable cut cylindrical elements generally aligned on a common axis and interconnected by one or more interconnective elements, the elements having a rectangular cross-section from cut-to-cut. The individual radially expandable cylindrical elements are disposed in an undulating pattern. The stent is manufactured by direct laser cutting from a single metal tube using a finely focused laser beam passing through a coaxial gas jet structure to impinge on the working surface of the tube as the linear and rotary velocity of the tube is precisely controlled.

3 Claims, 7 Drawing Sheets

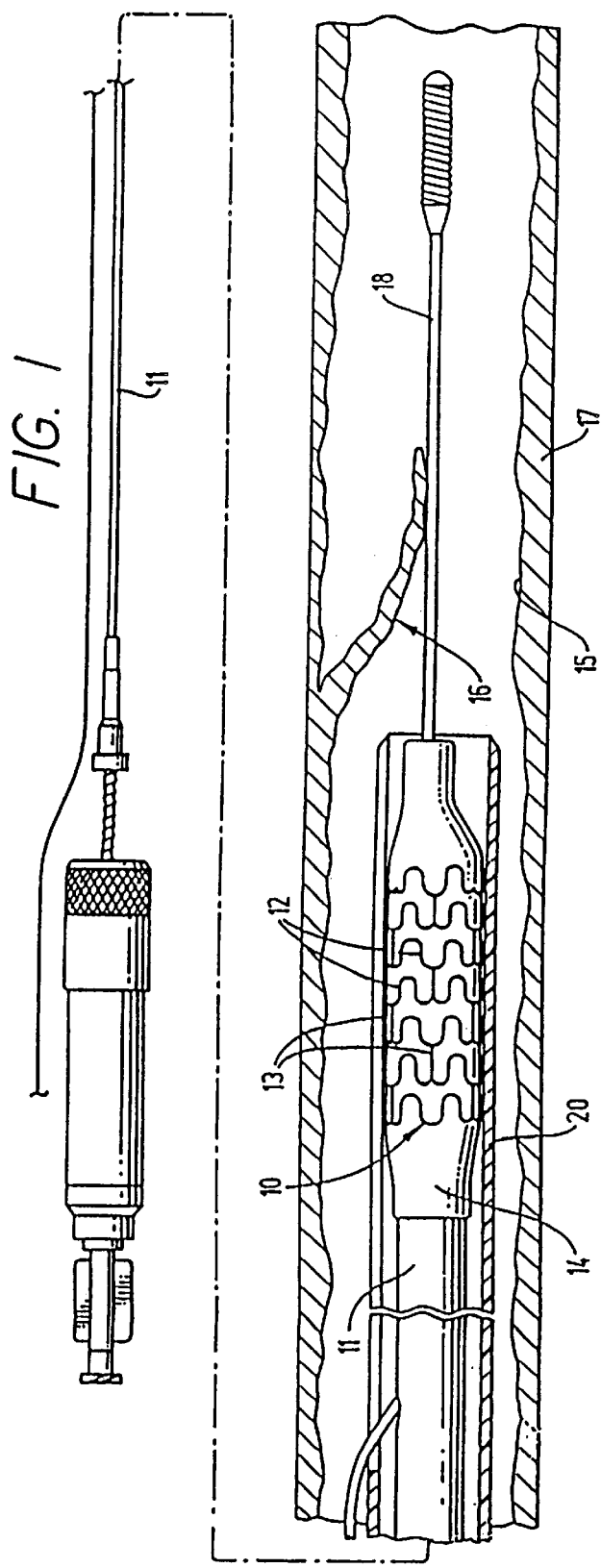
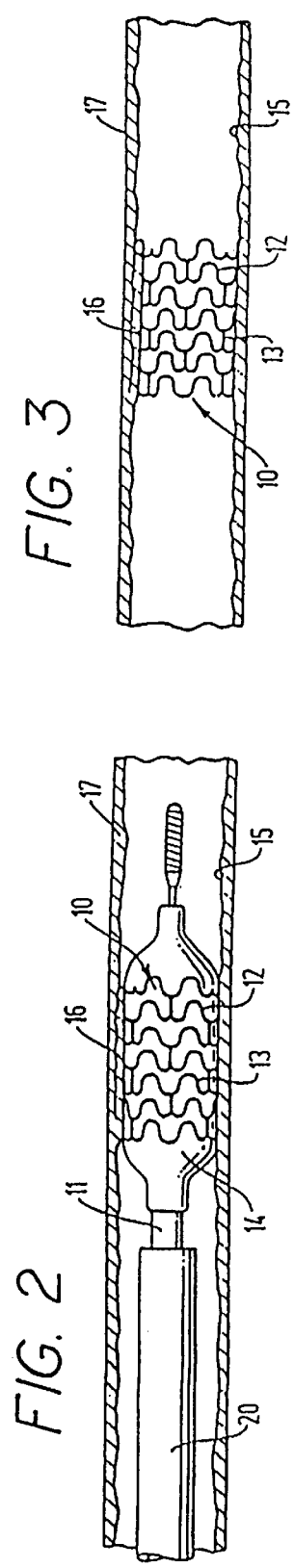

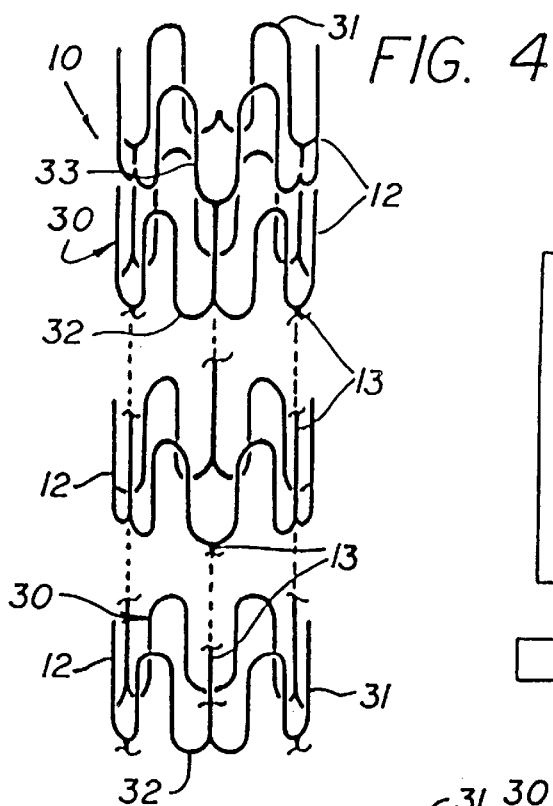
FIG. 4
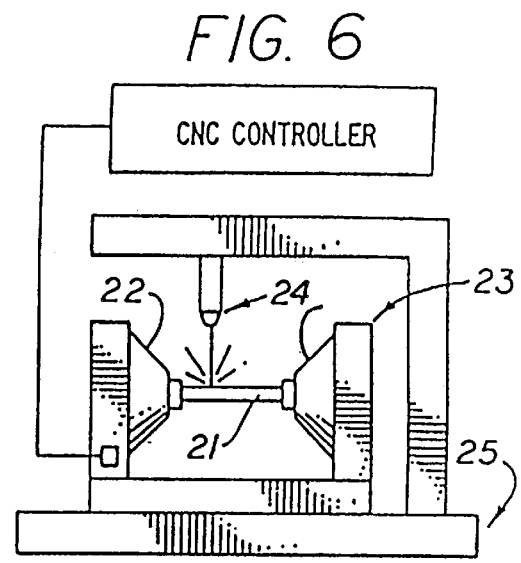
FIG. 6
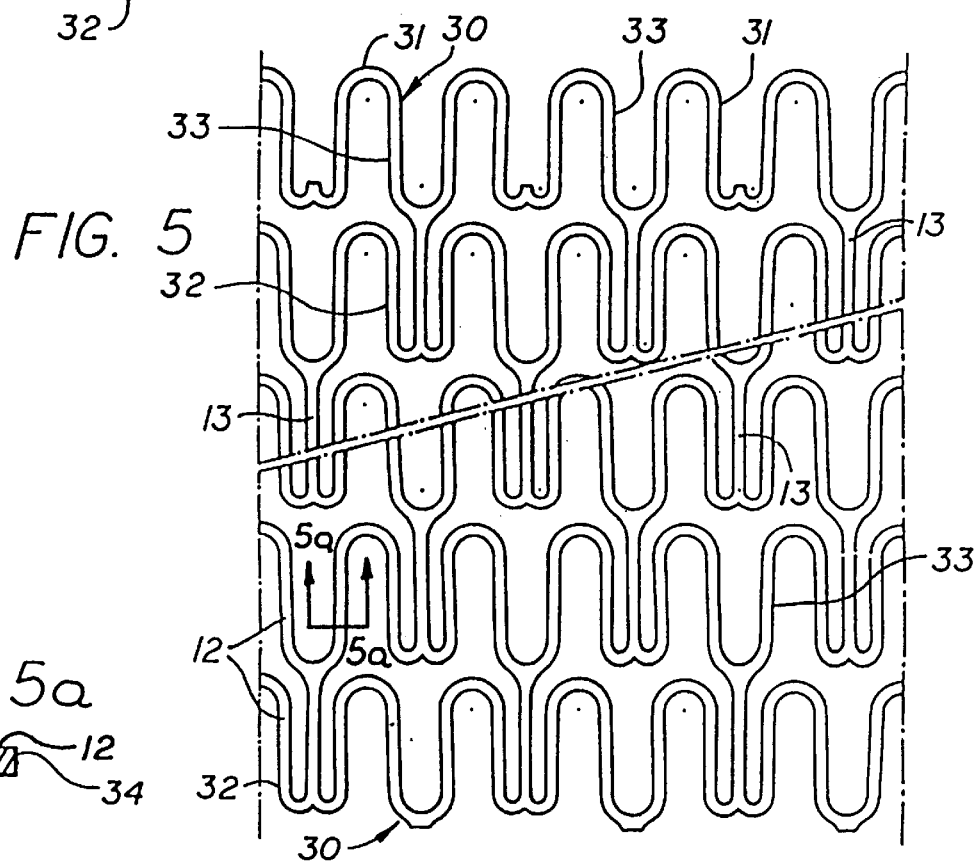
FIG. 5
FIG. 5a

COAXIAL GAS JET — ROTARY COLLECT AND
TUBE SUPPORT — TUBE BEAM BLOCK

BEAM DIAMETER VS SPOT SIZE AND DEPTH OF FOCUS

FOCAL LENGTH VS SPOT SIZE AND DEPTH OF FOCUS

METHOD AND APPARATUS FOR DIRECT LASER CUTTING OF METAL STENTS

This application is a Div. of 08/783,698, Jan. 15, 1997, U.S. Pat. No. 5,780,807, which is a con. of Ser. No. 08/345,501, Nov. 28, 1994, abn.

BACKGROUND OF THE INVENTION

This invention relates generally to improvements in the manufacture of expandable metal stents and, more particularly, to new and improved methods and apparatus for direct laser cutting of metal stents and providing stents of enhanced structural quality.

Stents are expandable endoprosthesis devices which are adapted to be implanted into a patient's body lumen, such as a blood vessel, to maintain the patency of the vessel. These devices are typically used in the treatment of atherosclerotic stenosis in blood vessels and the like.

In the medical arts, stents are generally tubular-shaped devices which function to hold open a segment of a blood vessel or other anatomical lumen. They are particularly suitable for use to support and hold back a dissected arterial lining which can occlude the fluid passageway.

Various means have been provided to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter.

One example of a particularly useful expandable stent is a stent which is relatively flexible along its longitudinal axis to facilitate delivery through tortuous body lumens, but which is stiff and stable enough radially in an expanded condition to maintain the patency of a body lumen such as an artery when implanted within the lumen. Such a desirable stent typically includes a plurality of radially expandable cylindrical elements which are relatively independent in their ability to expand and to flex relative to one another. The individual radially expandable cylindrical elements of the stent are precisely dimensioned so as to be longitudinally shorter than their own diameters. Interconnecting elements or struts extending between adjacent cylindrical elements provide increased stability and a preferable position to prevent warping of the stent when it is expanded. The resulting stent structure is a series of radially expandable cylindrical elements which are spaced longitudinally close enough so that small dissections in the wall of a body lumen may be pressed back into position against the lumenal wall, but not so close as to compromise the longitudinal flexibilities of the stent. The individual cylindrical elements may rotate slightly relative to adjacent cylindrical elements without significant deformation, cumulatively giving a stent which is flexible along its length and about its longitudinal axis, but is still very stiff in the radial direction in order to resist collapse.

The aforedescribed stents generally have a precisely layed out circumferential undulating pattern, e.g. serpentine. The transverse cross-section of the undulating component of the cylindrical element is relatively small and preferably has an apect ratio of about two to one to about 0.5 to one. A one to one apect ratio has been found particularly suitable. The open reticulated structure of the stent allows for the perfusion of blood over a large portion of the arterial wall which can improve the healing and repair of a damaged arterial lining.

The radial expansion of the expandable cylinder deforms the undulating pattern similar to changes in a waveform which result from decreasing the waveform's amplitude and the frequency. Preferably, the undulating patterns of the individual cylindrical structures are in phase with each other in order to prevent the contraction of the stent along its length when it is expanded. The cylindrical structures of the stent are plastically deformed when expanded so that the stent will remain in the expanded condition and, therefore, they must be sufficiently rigid when expanded to prevent their collapse in use. During expansion of the stent, portions of the undulating pattern will tip outwardly resulting in projecting members on the outer surface of the expanded stent. These projecting members tip radially outwardly from the outer surface of the stent and embed in the vessel wall and help secure the expanded stent so that it does not move once it is implanted.

The elongated elements which interconnect adjacent cylindrical elements should have a precisely defined transverse cross-section similar to the transverse dimensions of the undulating components of the expandable cylindrical elements. The interconnecting elements may be formed as a unitary structure with the expandable cylindrical elements from the same intermediate product, such as a tubular element, or they may be formed independently and connected by suitable means, such as by welding or by mechanically securing the ends of the interconnecting elements to the ends of the expandable cylindrical elements. Preferably, all of the interconnecting elements of a stent are joined at either the peaks or the valleys of the undulating structure of the cylindrical elements which form the stent. In this manner, there is no shortening of the stent upon expansion.

The number and location of elements interconnecting adjacent cylindrical elements can be varied in order to develop the desired longitudinal flexibility in the stent structure both in the unexpanded, as well as the expanded condition. These properties are important to minimize alteration of the natural physiology of the body lumen into which the stent is implanted and to maintain the compliance of the body lumen which is internally supported by the stent. Generally, the greater the longitudinal flexibility of the stent, the easier and the more safely it can be delivered to the implantation site.

It will be apparent from the foregoing that conventional stents are very high precision, relatively fragile devices and, ideally, the most desirable metal stents incorporate a fine precision structure cut from a very small diameter, thin-walled cylindrical tube. In this regard, it is extremely important to make precisely dimensioned, smooth, narrow cuts in the stainless tubes in extremely fine geometries without damaging the narrow struts that make up the stent structure. While the various cutting processes, including chemical etching, heretofore utilized by the prior art to form such expandable metal stents, have been adequate, improvements have been sought to provide stents of enhanced structural quality in terms of resolution, reliability and yield.

Accordingly, those concerned with the development, manufacture and use of metal stents have long recognized the need for improved manufacturing processes for such stents. The present invention fulfills these needs.

SUMMARY OF THE INVENTION

Briefly, and in general terms, the present invention provides a new and improved method and apparatus for direct laser cutting of metal stents enabling greater precision, reliability, structural integrity and overall quality, without burrs, slag or other imperfections which might otherwise hamper stent integrity and performance.

Basically, the present invention provides an improved system for producing metal stents with a fine precision structure cut from a small diameter, thin-walled, cylindrical tube. The tubes are typically made of stainless steel and are fixtured under a laser and positioned utilizing a CNC to generate a very intricate and precise pattern. Due to the thin-wall and the small geometry of the stent pattern, it is necessary to have very precise control of the laser, its power level, the focus spot size, and the precise positioning of the laser cutting path.

In a presently preferred embodiment of the invention, in order to minimize the heat input, which prevents thermal distortion, uncontrolled burn out of the metal, and metallurgical damage due to excessive heat, a Q-switched Nd/YAG laser that is frequency doubled to produce a green beam at 532 nanometers is utilized. Q-switching produces very short pulses (<100 nS) of high peak powers (kilowatts), low energy per pulse ($\leqq 3$ mJ), at high pulse rates (up to 40 kHz). The frequency doubling of the beam from 1.06 microns to 0.532 microns allows the beam to be focused to a spot size that is 2 times smaller and, therefore, increases the power density by a factor of four. With all of these parameters, it is possible to make smooth, narrow cuts in the stainless tubes in very fine geometries without damaging the narrow struts that make up to stent structure.

In addition to the laser and the CNC positioning equipment, the optical delivery system utilized in the practice of the present invention, includes a beam expander to increase the laser beam diameter, a circular polarizer to eliminate polarization effects in metal cutting, provisions for a spatial filter, a binocular viewing head and focusing lens, and a coaxial gas jet that provides for the introduction of a gas stream that surrounds the focused beam and is directed along the beam axis. The coaxial gas jet nozzle is centered around the focused beam with approximately 0.010" between the tip of the nozzle and the tubing. The jet is pressurized with oxygen at 20 psi and is directed at the tube with the focused laser beam exiting the tip of the nozzle. The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube inside diameter, a stainless steel mandrel is placed inside the tube and is allowed to roll on the bottom of the tube as the pattern is cut. This acts as a beam/debris block protecting the far wall inside diameter.

The cutting process utilizing oxygen with the finely focused green beam results in a very narrow kerf (approx. 0.0005") with the molten slag re-solidifying along the cut. This traps the cut out scrap of the pattern and requires further processing. In order to remove the slag debris from the cut allowing the scrap to be removed from the remaining stent pattern, it is desirable to soak the cut tube in a solution of HCL for a selected time and temperature. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for a period of time dependent upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are then ready for electropolishing.

Hence, the new and improved method and apparatus for direct laser cutting of metal stents, in accordance with the present invention, makes accurate, reliable, high resolution, expandable stents with patterns having smooth, narrow cuts and very fine geometries.

The above and other objects and advantages of this invention will be apparent from the following more detailed description when taken in conjunction with the accompanying drawings of exemplary embodiments.

DESCRIPTION OF THE DRAWINGS

FIG. 1 is an elevational view, partially in section, of a stent embodying features of the invention which is mounted on a delivery catheter and disposed within a damaged artery;

FIG. 2 is an elevational view, partially in section, similar to that shown in FIG. 1 wherein the stent is expanded within a damaged artery, pressing the damaged lining against the arterial wall;

FIG. 3 is an elevational view, partially in section showing the expanded stent within the artery after withdrawal of the delivery catheter;

FIG. 4 is a perspective view of a stent embodying in an unexpanded state, with one end of the stent being shown in an exploded view to illustrate the details thereof;

FIG. 5 is a plan view of a flattened section of a stent of the invention which illustrates the undulating pattern of the stent shown in FIG. 4;

FIG. 5a is a sectional view taken along the line 5a–5a in FIG. 5;

FIG. 6 is a schematic representation of equipment for selectively cutting the tubing in the manufacture of stents, in accordance with the present invention;

DETAILED DESCRIPTION OF THE PREFERRED EMBODIMENTS

Figure 7:
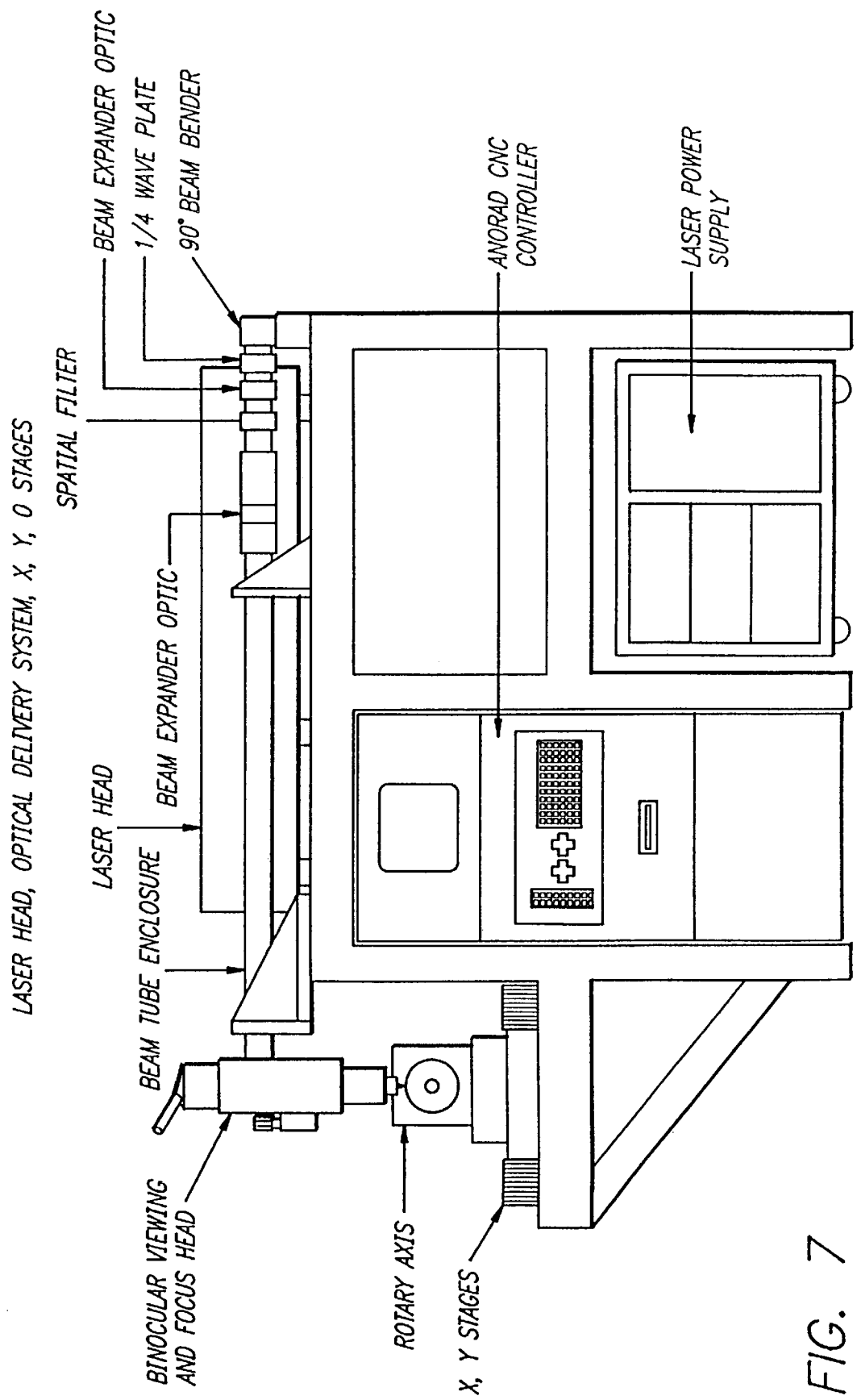
FIG. 7 is an elevational view of a system for cutting an appropriate pattern by laser in a metal tube to form a stent, in accordance with the invention.
Figure 8:
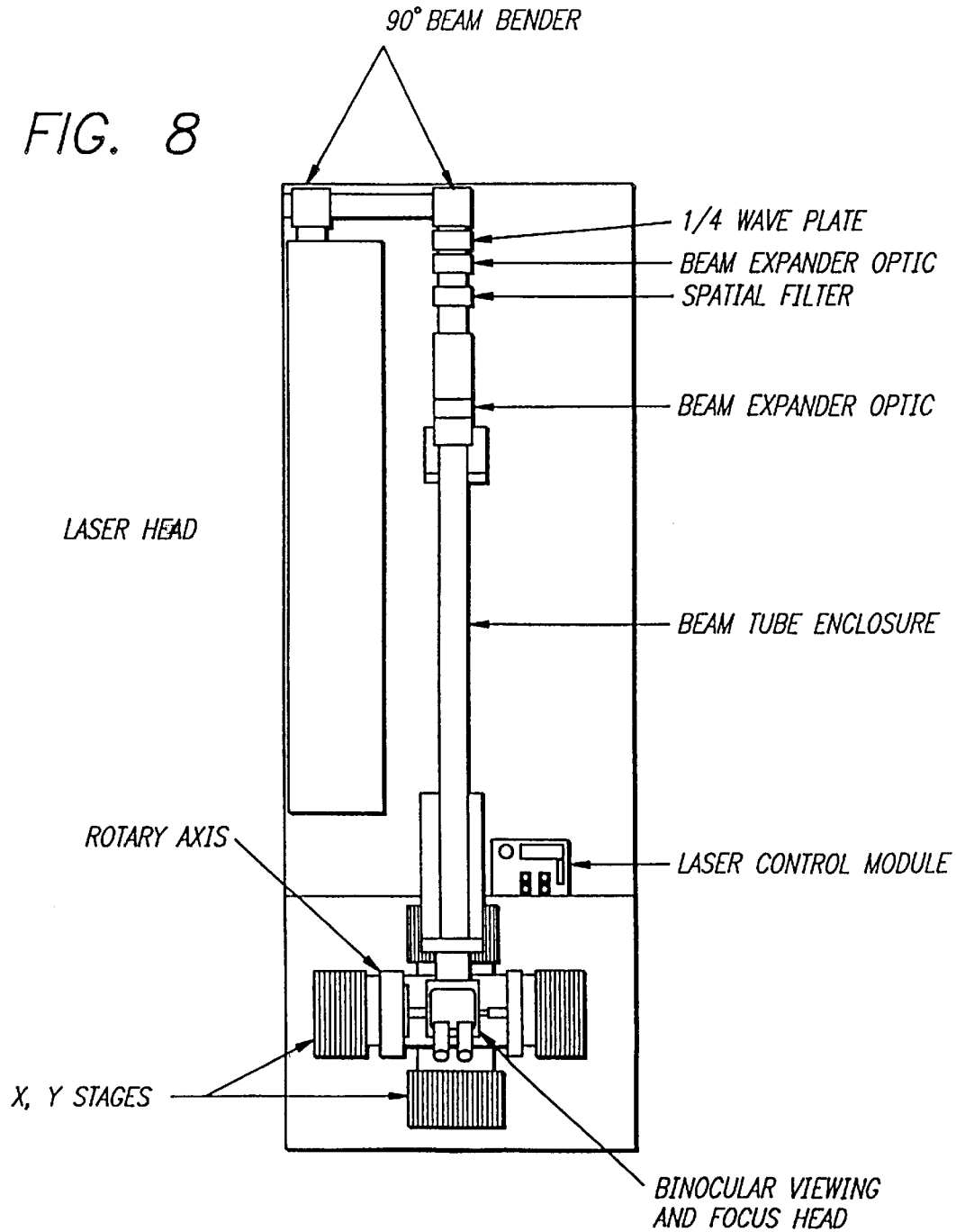
FIG. 8 is a plan view of the laser head and optical delivery subsystem for the laser cutting system shown in FIG. 7.
Figure 9:
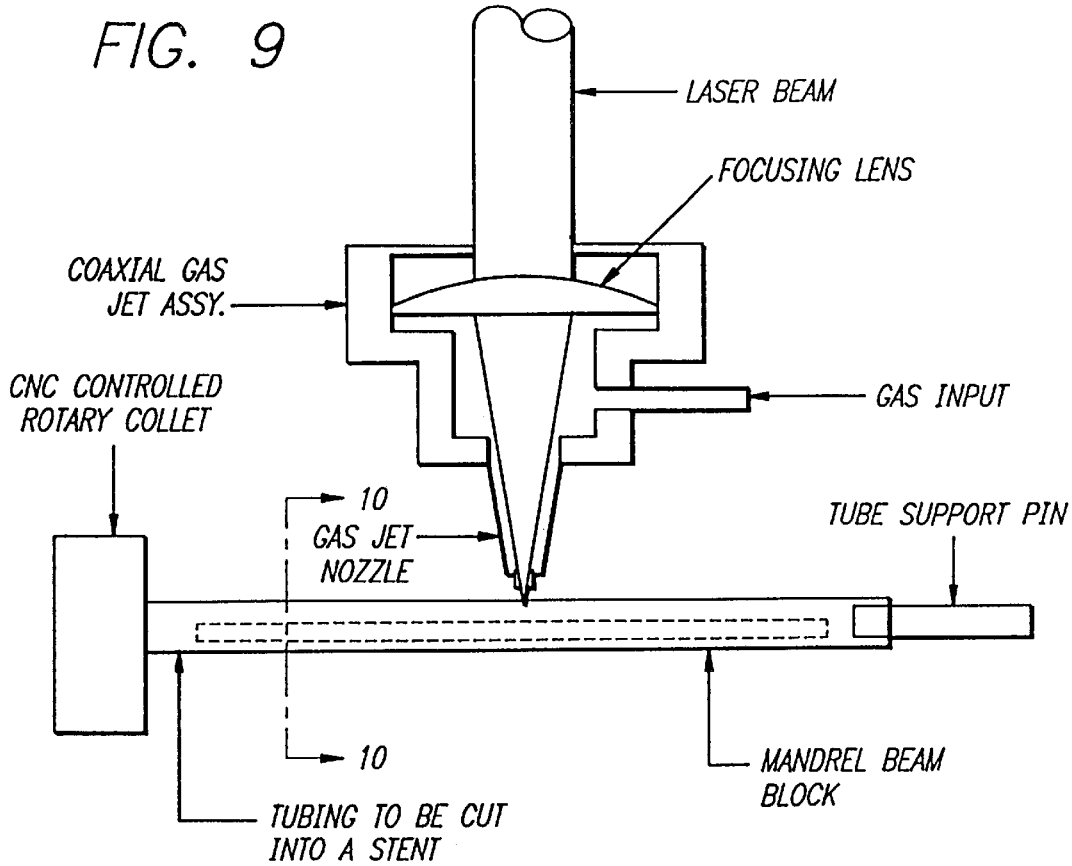
FIG. 9 is an elevational view of a coaxial gas jet, rotary collet, tube support and beam blocking apparatus for use in the system of FIG. 7.
Figure 10:
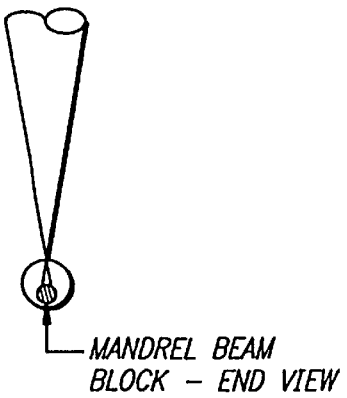
FIG. 10 is a sectional view taken along the line 10—10 in FIG. 9.

Referring now to the drawings, and particularly FIG. 1 thereof, there is shown a stent 10 which is mounted onto a delivery catheter 11. The stent 10 is a high precision patterned tubular device. The stent 10 typically comprises a plurality of radially expanded cylindrical elements 12 disposed generally coaxially and interconnected by elements 13 disposed between adjacent cylindrical elements. The delivery catheter 11 has an expandable portion or balloon 14 for expanding of the stent 10 within an artery 15. The artery 15, as shown in FIG. 1 has a dissected lining 16 which has occluded a portion of the arterial passageway.

The typical delivery catheter 11 onto which the stent 10 is mounted, is essentially the same as a conventional balloon dilatation catheter for angioplasty procedures. The balloon 14 may be formed of suitable materials such as polyethylene, polyethylene terephthalate, polyvinyl chloride, nylon and ionomers such as Surlyn® manufactured by the Polymer Products Division of the Du Pont Company. Other polymers may also be used. In order for the stent 10 to remain in place on the balloon 14 during delivery to the site of the damage within the artery 15, the stent 10 is compressed onto the balloon. A retractable protective delivery sleeve 20 as described in copending application Ser. No. 07/647,464 filed on Apr. 25, 1990 and entitled STENT DELIVERY SYSTEM may be provided to further ensure that the stent stays in place on the expandable portion of the delivery catheter 11 and prevent abrasion of the body lumen by the open surface of the stent 20 during delivery to the desired arterial location. Other means for securing the stent 10 onto the balloon 14 may also be used, such as providing collars or ridges on the ends of the working portion, i.e. the cylindrical portion, of the balloon.

Each radially expandable cylindrical element 12 of the stent 10 may be independently expanded. Therefore, the balloon 14 may be provided with an inflated shape other than cylindrical, e.g. tapered, to facilitate implantation of the stent 10 in a variety of body lumen shapes.

The delivery of the stent 10 is accomplished in the following manner. The stent 10 is first mounted onto the inflatable balloon 14 on the distal extremity of the delivery catheter 11. The balloon 14 is slightly inflated to secure the stent 10 onto the exterior of the balloon. The catheter-stent assembly is introduced within the patient's vasculature in a conventional Seldinger technique through a guiding catheter (not shown). A guidewire 18 is disposed across the damaged arterial section with the detached or dissected lining 16 and then the catheter-stent assembly is advanced over a guidewire 18 within the artery 15 until the stent 10 is directly under the detached lining 16. The balloon 14 of the catheter is expanded, expanding the stent 10 against the artery 15, which is illustrated in FIG. 2. While not shown in the drawing, the artery 15 is preferably expanded slightly by the expansion of the stent 10 to seat or otherwise fix the stent 10 to prevent movement. In some circumstances during the treatment of stenotic portions of an artery, the artery may have to be expanded considerably in order to facilitate passage of blood or other fluid therethrough.

The stent 10 serves to hold open the artery 15 after the catheter 11 is withdrawn, as illustrated by FIG. 3. Due to the formation of the stent 10 from elongated tubular member, the undulating component of the cylindrical elements of the stent 10 is relatively flat in transverse cross-section, so that when the stent is expanded, the cylindrical elements are pressed into the wall of the artery 15 and as a result do not interfere with the blood flow through the artery 15. The cylindrical elements 12 of the stent 10 which are pressed into the wall of the artery 15 will eventually be covered with endothelial cell growth which further minimizes blood flow interference. The undulating portion of the cylindrical sections 12 provide good tacking characteristics to prevent stent movement within the artery. Furthermore, the closely spaced cylindrical elements 12 at regular intervals provide-uniform support for the wall of the artery 15, and consequently are well adapted to tack up and hold in place small flaps or dissections in the wall of the artery 15, as illustrated in FIGS. 2 and 3.

FIG. 4 is an enlarged perspective view of the stent 10 shown in FIG. 1 with one end of the stent shown in an exploded view to illustrate in greater detail the placement of interconnecting elements 13 between adjacent radially expandable cylindrical elements 12. Each pair of the interconnecting elements 13 on one side of a cylindrical element 12 are preferably placed to achieve maximum flexibility for a stent. In the embodiment shown in FIG. 4, the stent 10 has three interconnecting elements 13 between adjacent radially expandable cylindrical elements 12 which are 120° apart. Each pair of interconnecting elements 13 on one side of a cylindrical element 12 are offset radially 60° from the pair on the other side of the cylindrical element. The alternation of the interconnecting elements results in a stent which is longitudinally flexible in essentially all directions. Various configurations for the placement of interconnecting elements are possible. However, as previously mentioned, all of the interconnecting elements of an individual stent should be secured to either the peaks or valleys of the undulating structural elements in order to prevent shortening of the stent during the expansion thereof.

The number of undulations may also be varied to accommodate placement of interconnecting elements 13, e.g. at the peaks of the undulations or along the sides of the undulations as shown in FIG. 5.

As best observed in FIGS. 4 and 5, cylindrical elements 12 are in the form of a serpentine pattern 30. As previously mentioned, each cylindrical element 12 is connected by interconnecting elements 13. Serpentine pattern 30 is made up of a plurality of U-shaped members 31, W-shaped members 32, and Y-shaped members 33, each having a different radius so that expansion forces are more evenly distributed over the various members.

The afordescribed illustrative stent 10 and similar stent structures can be made in many ways. However, the preferred method of making the stent is to cut a thin-walled tubular member, such as stainless steel tubing to remove portions of the tubing in the desired pattern for the stent, leaving relatively untouched the portions of the metallic tubing which are to form the stent. In accordance with the invention, it is preferred to cut the tubing in the desired pattern by means of a machine-controlled laser as illustrated schematically in FIG. 6.

The tubing may be made of suitable biocompatible material such as stainless steel. The stainless steel tube may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent.

| | |
|---|---|
| Carbon (C) | 0.03% max. |
| Manganese (Mn) | 2.00% max. |
| Phosphorous (P) | 0.025% max. |
| Sulphur (S) | 0.010% max. |
| Silicon (Si) | 0.75% max. |
| Chromium (Cr) | 17.00–19.00% |
| Nickel (Ni) | 13.00–15.50% |
| Molybdenum (Mo) | 2.00–3.00% |
| Nitrogen (N) | 0.10% max. |
| Copper (Cu) | 0.50% max. |
| Iron (Fe) | Balance |

The stent diameter is very small, so the tubing from which it is made must necessarily also have a small diameter. Typically the stent has an outer diameter on the order of about 0.06 inch in the unexpanded condition, the same outer diameter of the tubing from which it is made, and can be expanded to an outer diameter of 0.1 inch or more. The wall thickness of the tubing is about 0.003 inch.

Referring to FIG. 6, the tubing 21 is put in a rotatable collet fixture 22 of a machine-controlled apparatus 23 for positioning the tubing 21 relative to a laser 24. According to machine-encoded instructions, the tubing 21 is rotated and moved longitudinally relative to the laser 24 which is also machine-controlled. The laser selectively removes the material from the tubing by ablation and a pattern is cut into the tube. The tube is therefore cut into the discrete pattern of the finished stent.

The process of cutting a pattern for the stent into the tubing is automated except for loading and unloading the length of tubing. Referring again to FIG. 6 it may be done, for example, using a CNC-opposing collet fixture 22 for axial rotation of the length of tubing, in conjunction with a CNC X/Y table 25 to move the length of tubing axially relatively to a machine-controlled laser as described. The entire space between collets can be patterned using the $CO_2$ laser set-up of the foregoing example. The program for control of the apparatus is dependent on the particular configuration used and the pattern to be ablated in the coating.

Referring now to FIGS. 7–10 of the drawings, there is shown a process and apparatus, in accordance with the invention, for producing metal stents with a fine precision structure cut from a small diameter thin-walled cylindrical tube. Cutting a fine structure (0.0035" web width) requires minimal heat input and the ability to manipulate the tube with precision. It is also necessary to support the tube yet not allow the stent structure to distort during the cutting operation. In order to successfully achieve the desired end results, the entire system must be configured very carefully. The tubes are made of stainless steel with an outside diameter of 0.060" to 0.066" and a wall thickness of 0.002" to 0.004". These tubes are fixtured under a laser and positioned utilizing a CNC to generate a very intricate and precise pattern. Due to the thin wall and the small geometry of the stent pattern (0.0035" typical web width), it is necessary to have very precise control of the laser, its power level, the focused spot size, and the precise positioning of the laser cutting path.

In order to minimize the heat input into the stent structure, which prevents thermal distortion, uncontrolled burn out of the metal, and metallurgical damage due to excessive heat, and thereby produce a smooth debris free cut, a Q-switched Nd/YAG, typically available from Quantronix of Hauppauge, New York, that is frequency doubled to produce a green beam at 532 nanometers is utilized. Q-switching produces very short pulses (<100 nS) of high peak powers (kilowatts), low energy per pulse ($\leq$3 mJ), at high pulse rates (up to 40 kHz). The frequency doubling of the beam from 1.06 microns to 0.532 microns allows the beam to be focused to a spot size that is 2 times smaller, therefore increasing the power density by a factor of 4 times. With all of these parameters, it is possible to make smooth, narrow cuts in the stainless tubes in very fine geometries without damaging the narrow struts that make up to stent structure. Hence, the system of the present invention makes it possible to adjust the laser parameters to cut narrow kerf width which will minimize the heat input into the material.

The positioning of the tubular structure requires the use of precision CNC equipment such as that manufactured and sold by Anorad Corporation. In addition, a unique rotary mechanism has been provided that allows the computer program to be written as if the pattern were being cut from a flat sheet. This allows both circular and linear interpolation to be utilized in programming. Since the finished structure of the stent is very small, a precision drive mechanism is required that supports and drives both ends of the tubular structure as it is cut. Since both ends are driven, they must be aligned and precisely synchronized, otherwise the stent structure would twist and distort as it is being cut. A suitable computer program for controlling the CNC equipment is enclosed herewith as Appendix A.

The optical system which expands the original laser beam, delivers the beam through a viewing head and focuses the beam onto the surface of the tube, incorporates a coaxial gas jet and nozzle that helps to remove debris from the kerf and cools the region where the beam interacts with the material as the beam cuts and vaporizes the metal. It is also necessary to block the beam as it cuts through the top surface of the tube and prevent the beam, along with the molten metal and debris from the cut, from impinging on the opposite surface of the tube.

In addition to the laser and the CNC positioning equipment, the optical delivery system includes a beam expander to increase the laser beam diameter, a circular polarizer, typically in the form of a quarter wave plate, to eliminate polarization effects in metal cutting, provisions for a spatial filter, a binocular viewing head and focusing lens, and a coaxial gas jet that provides for the introduction of a gas stream that surrounds the focused- beam and is directed along the beam axis. The coaxial gas jet nozzle (0.018" I.D.) is centered around the focused beam with approximately 0.010" between the tip of the nozzle and the tubing. The jet is pressurized with oxygen at 20 psi and is directed at the tube with the focused laser beam exiting the tip of the nozzle (0.018" dia.) The oxygen reacts with the metal to assist in the cutting process very similar to oxyacetylene cutting. The focused laser beam acts as an ignition source and controls the reaction of the oxygen with the metal. In this manner, it is possible to cut the material with a very fine kerf with precision. In order to prevent burning by the beam and/or molten slag on the far wall of the tube I.D., a stainless steel mandrel (approx. 0.034" dia.) is placed inside the tube and is allowed to roll on the bottom of the tube as the pattern is cut. This acts as a beam/debris block protecting the far wall I.D.

Alternatively, this may be accomplished by inserting a second tube inside the stent tube which has an opening to trap the excess energy in the beam which is transmitted through the kerf along which collecting the debris that is ejected from the laser cut kerf. A vacuum or positive pressure can be placed in this shielding tube to remove the collection of debris.

Another technique that could be utilized to remove the debris from the kerf and cool the surrounding material would be to use the inner beam blocking tube as an internal gas jet. By sealing one end of the tube and making a small hole in the side and placing it directly under the focused laser beam, gas pressure could be applied creating a small jet that would force the debris out of the laser cut kerf from the inside out. This would eliminate any debris from forming or collecting on the inside of the stent structure. It would place all the debris on the outside. With the use of special protective coatings, the resultant debris can be easily removed.

In most cases, the gas utilized in the jets may be reactive or non-reactive (inert). In the case of reactive gas, oxygen or compressed air is used. Compressed air is used in this application since it offers more control of the material removed and reduces the thermal effects of the material itself. Inert gas such as argon, helium, or nitrogen can be used to eliminate any oxidation of the cut material. The result is a cut edge with no oxidation, but there is usually a tail of molten material that collects along the exit side of the gas jet that must be mechanically or chemically removed after the cutting operation.

The cutting process utilizing oxygen with the finely focused green beam results in a very narrow kerf (approx. 0.0005") with the molten slag re-solidifying along the cut. This traps the cut out scrap of the pattern requiring further processing. In order to remove the slag debris from the cut allowing the scrap to be removed from the remaining stent pattern, it is necessary to soak the cut tube in a solution of HCL for approximately 8 minutes at a temperature of approximately 55° C. Before it is soaked, the tube is placed in a bath of alcohol/water solution and ultrasonically cleaned for approximately 1 minute to remove the loose debris left from the cutting operation. After soaking, the tube is then ultrasonically cleaned in the heated HCL for 1–4 minutes depending upon the wall thickness. To prevent cracking/breaking of the struts attached to the material left at the two ends of the stent pattern due to harmonic oscillations induced by the ultrasonic cleaner, a mandrel is placed down the center of the tube during the cleaning/scrap removal process. At completion of this process, the stent structures are rinsed in water. They are now ready for electropolishing.

The stents are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110–135° F. and the current density is about 0.4 to about 1.5 amps per in.$^2$. Cathode to anode area should be at least about two to one. The stents may be further treated if desired, for example by applying a biocompatible coating.

Figure 11:
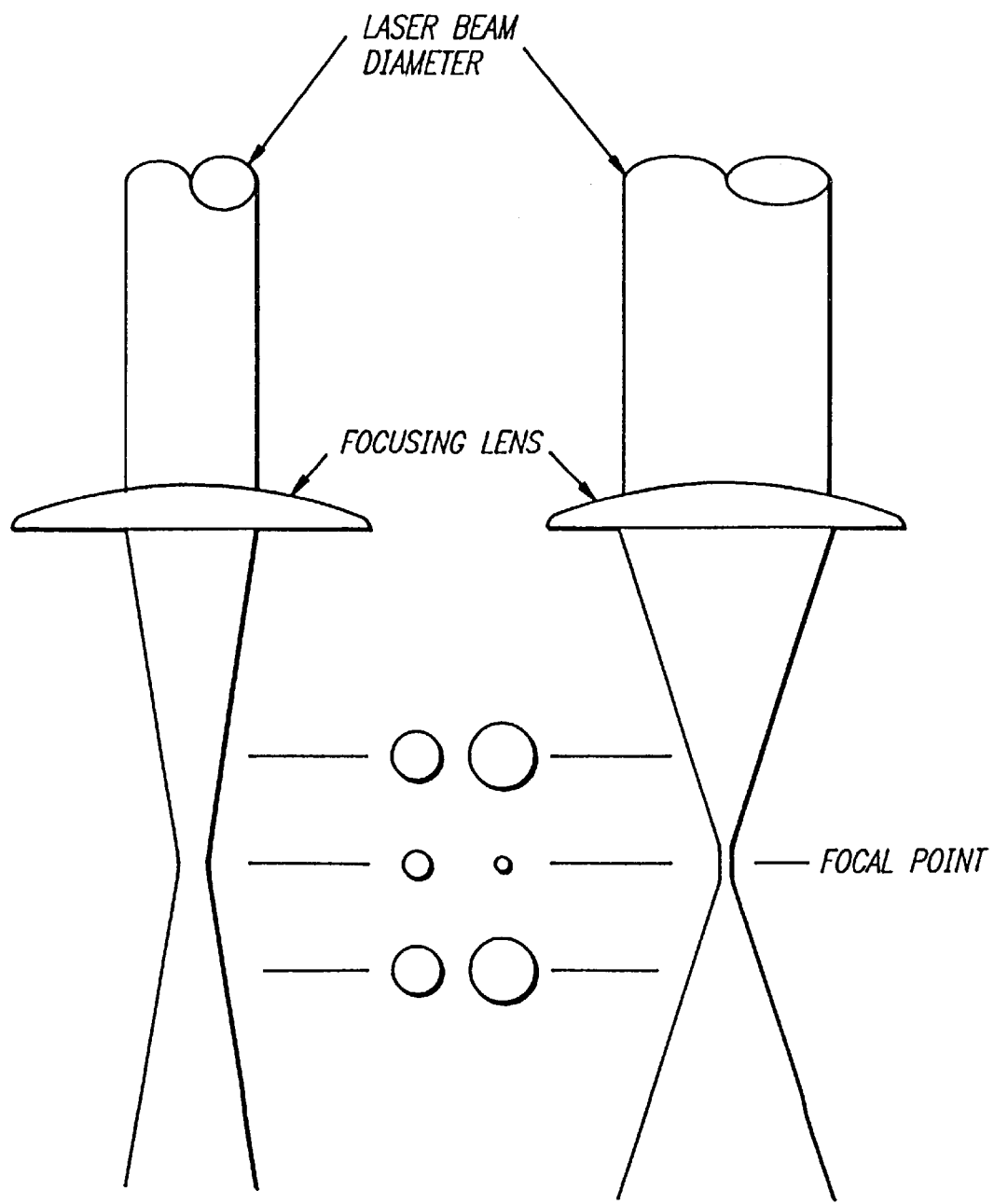
FIG. 11 is an elevational and schematic drawing of laser beam diameter vs. spot size and depth of focus.
Figure 12:
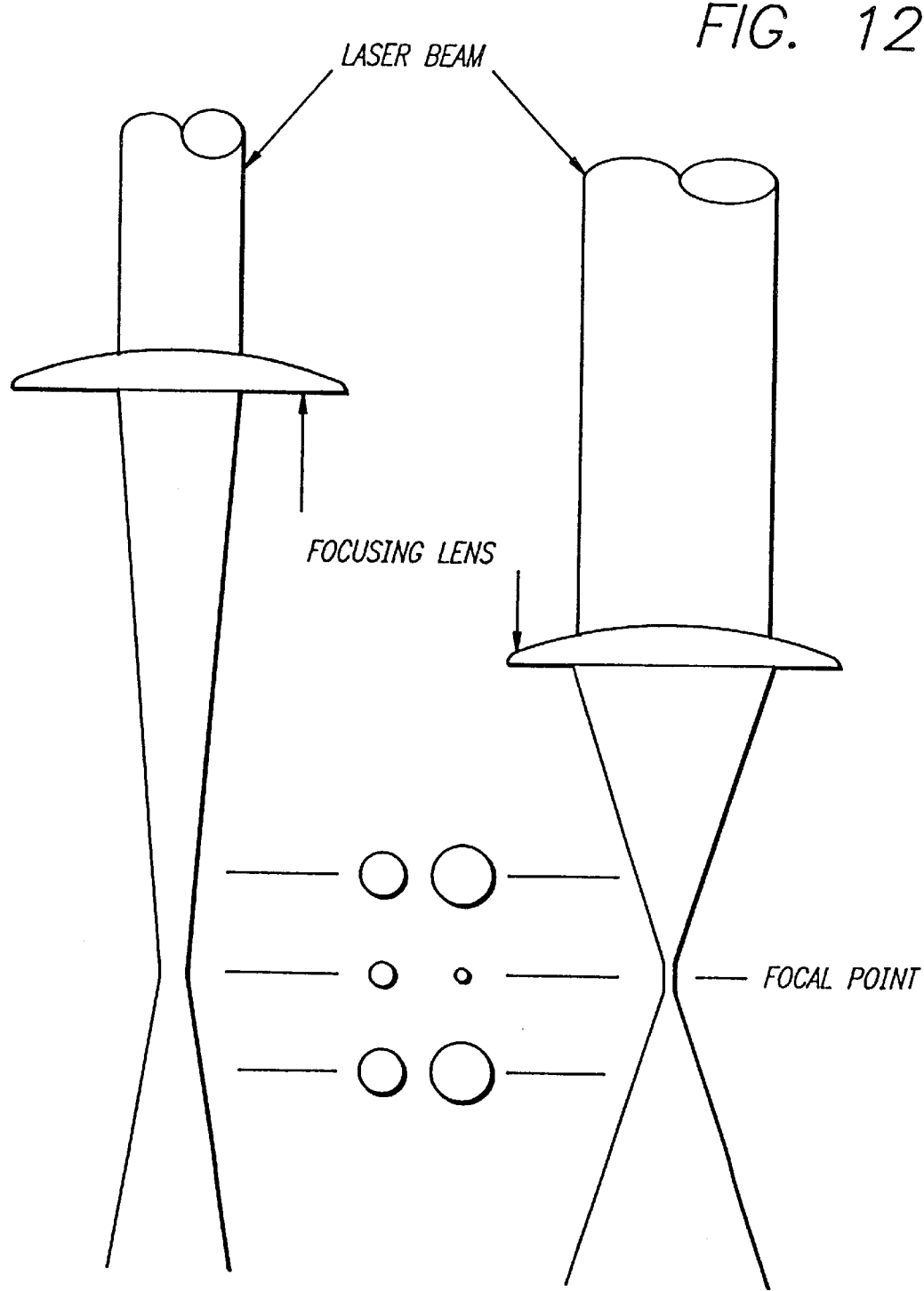
FIG. 12 is an elevational and schematic drawing of focal length vs. spot size and depth of focus.

Referring now more particularly to FIGS. 11 and 12, it will be apparent that both focused laser spot size and depth of focus can be controlled by selecting beam diameter (FIG. 11) and focal length for the focusing lens (FIG. 12). It will be apparent from FIGS. 11 and 12 that increasing laser beam diameter, or reducing lens focal length, reduces spot size at the cost of depth of field.

Direct laser cutting produces edges which are essentially perpendicular to the axis of the laser cutting beam, in contrast with chemical etching and the like which produce pattern edges which are angled. Hence, the laser cutting process of the present invention essentially provides stent cross-sections, from cut-to-cut, which are square or rectangular, rather than trapezoidal; see FIG. 5a. The resulting stent structure provides superior performance.

It will be apparent from the foregoing that the present invention provides a new and improved method and apparatus for direct laser cutting of metal stents enabling greater precision, reliability, structural integrity and overall quality, without burrs, slag or other imperfections which might otherwise hamper stent integrity and performance. While the invention has been illustrated and described herein in terms of its use as an intravascular stent, it will be apparent to those skilled in the art that the stent can be used in other instances such as to expand prostatic urethras in cases of prostate hyperplasia. Other modifications and improvements may be made without departing from the scope of the invention.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A method of producing a stent, comprising the steps of:

providing a tubular member having a working outer tube surface, an inner tube surface defining an inside diameter of the tubular member, and a tubular wall between the working outer tube surface and the inner tube surface;

the tubular wall having a substantially uniform thickness in the range of about 0.002 to 0.005 inch;

impinging a laser beam on the working outer tube surface thereby causing the laser beam to cut through the tubular wall;

selecting a laser beam focal length to provide a kerf width about 0.0005 inch wide; and providing relative movement between the laser beam and the tubular member to cut a stent pattern.

2. The method of claim 1, wherein the laser beam forms molten slag and by applying a gas jet stream substantially surrounding the laser beam where the beam impinges on the working outer tube surface, the slag re-solidifying along the cut.

3. The method of claim 1, wherein the laser beam forms molten slag, the method comprising, after the providing relative movement step, the further step of chemically treating the stent to remove the slag and polish the outer tube surface and the inner tube surface.

* * * * *

UNITED STATES PATENT AND TRADEMARK OFFICE
CERTIFICATE OF CORRECTION

PATENT NO. : 6,131,266
DATED : October 17, 2000
INVENTOR(S) : Richard J. Saunders Page 1 of 1

It is certified that error appears in the above-identified patent and that said Letters Patent is hereby corrected as shown below:

Title page,
Under "FOREIGN PATENT DOCUMENTS", add the following patents:
-- 0 540 290 A2   5/1993    European Pat. Off.
   0 541 443 A1   5/1993    European Pat. Off.
   0 562 150 A1   9/1993    European Pat. Off.
   0 624 421 A3   11/1994   European Pat. Off.
   0 662 307 A1   7/1995    European Pat. Off.
   0 679 373 A2   11/1995   European Pat. Off. --.

Column 5,
Line 17, change "20", to read -- 10 --.

Signed and Sealed this

Fifth Day of March, 2002

*Attest:*

*Attesting Officer*

JAMES E. ROGAN
*Director of the United States Patent and Trademark Office*